United States Patent [19]

Finn et al.

[11] Patent Number: 5,667,472

[45] Date of Patent: Sep. 16, 1997

[54] SURGICAL INSTRUMENT AND METHOD FOR USE WITH A VIEWING SYSTEM

[75] Inventors: Miles A. Finn, Minneapolis; Thomas A. Poss, St. Louis Park; Craig L. Riedl, Long Lake; John C. Vanden Hoek, Elk River, all of Minn.

[73] Assignee: Clarus Medical Systems, Inc., Minneapolis, Minn.

[21] Appl. No.: 210,588

[22] Filed: Mar. 18, 1994

[51] Int. Cl.$^6$ ............ A61B 1/005; A61B 1/313
[52] U.S. Cl. ............ 600/104; 600/160; 600/139; 600/182; 606/170; 606/205
[58] Field of Search ............ 128/4–10, 751; 606/15, 16, 46, 167, 170, 205, 211, 207, 139, 140; 604/20; 433/29, 31; 600/101, 104, 113, 114, 153, 175, 182, 139; 362/32

[56] References Cited

U.S. PATENT DOCUMENTS

| | | | |
|---|---|---|---|
| 2,068,721 | 1/1937 | Wappler et al. | 606/46 |
| 2,539,828 | 1/1951 | Goldis et al. | 362/32 |
| 2,691,370 | 10/1954 | Wallace | 128/6 |
| 3,614,414 | 10/1971 | Gores | 362/32 |
| 3,758,951 | 9/1973 | Scrivo et al. | 362/32 |
| 3,882,854 | 5/1975 | Hulka et al. | 128/6 |
| 4,471,766 | 9/1984 | Terayama | 128/6 |
| 4,562,838 | 1/1986 | Walker | 604/22 |
| 4,588,294 | 5/1986 | Siegmund | 128/6 |
| 4,616,631 | 10/1986 | Takahashi | 128/6 |
| 4,620,547 | 11/1986 | Boebel | 128/4 X |
| 4,651,201 | 3/1987 | Schoolman | 128/6 X |
| 4,656,999 | 4/1987 | Storz | 128/4 |
| 4,759,348 | 7/1988 | Cawood | 128/6 |
| 5,016,098 | 5/1991 | Cooper et al. | 128/6 X |
| 5,152,779 | 10/1992 | Sanagi | 128/751 |
| 5,230,621 | 7/1993 | Jacoby | 433/29 |
| 5,281,134 | 1/1994 | Schultz | 433/29 |
| 5,312,400 | 5/1994 | Bales et al. | 606/46 X |
| 5,373,840 | 12/1994 | Knighton | 128/4 |
| 5,374,277 | 12/1994 | Hassler | 606/207 |

FOREIGN PATENT DOCUMENTS

| | | |
|---|---|---|
| 0 316 816 | 5/1989 | European Pat. Off. |
| 20 24 195 | 11/1970 | Germany. |
| 86 00 868 | 3/1986 | Germany. |
| 3920706 | 1/1991 | Germany ............ 600/182 |

OTHER PUBLICATIONS

English Translation of DE 20 24 195.
English Translation of DE 86 00 868.

*Primary Examiner*—Richard J. Apley
*Assistant Examiner*—John P. Leubecker
*Attorney, Agent, or Firm*—Olson & Hierl, Ltd.

[57] ABSTRACT

A surgical instrument for improved viewing of a surgical site by a surgeon from the perspective of a working element of the instrument. The surgical instrument includes an elongated shaft with a distal operating portion extending at least about one-fourth of the length of the shaft. A working element is disposed on a distal end of the shaft. An elongated fiberoptic assembly is included, having image fibers with a distal end with an objective lens for defining a predetermined field-of-view, and a coupling device at a proximal end for coupling same to a viewing system. A mounting device is utilized for mounting the fiberoptic assembly to the shaft along the length of the distal operating portion thereof. The distal end of the image fibers is positioned with a predetermined portion of the working element within the field-of-view of the fiberoptic assembly.

50 Claims, 8 Drawing Sheets

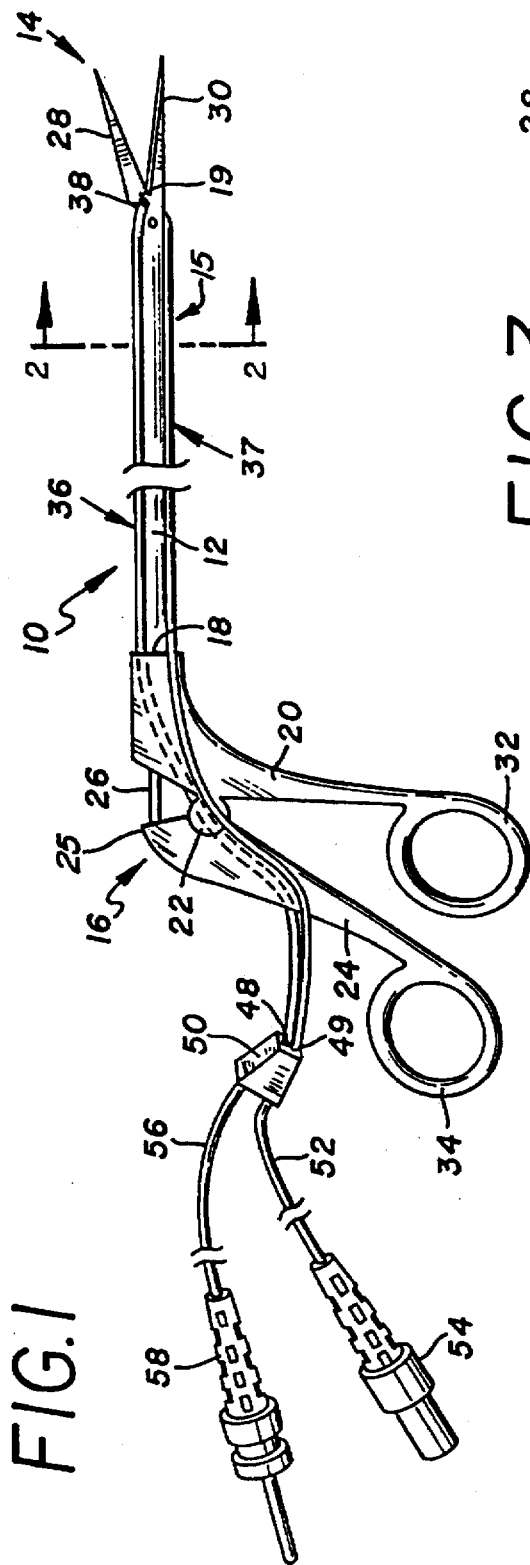
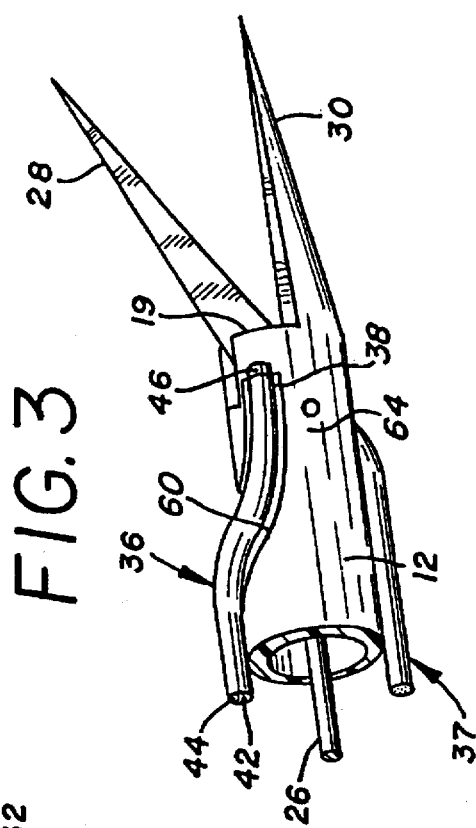
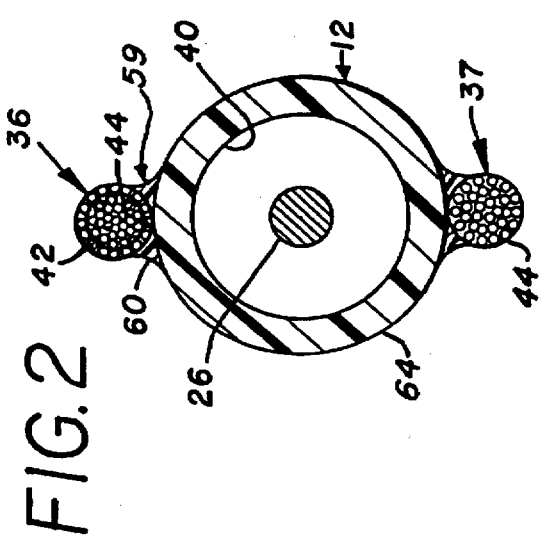
FIG. 1
FIG. 3
FIG. 2

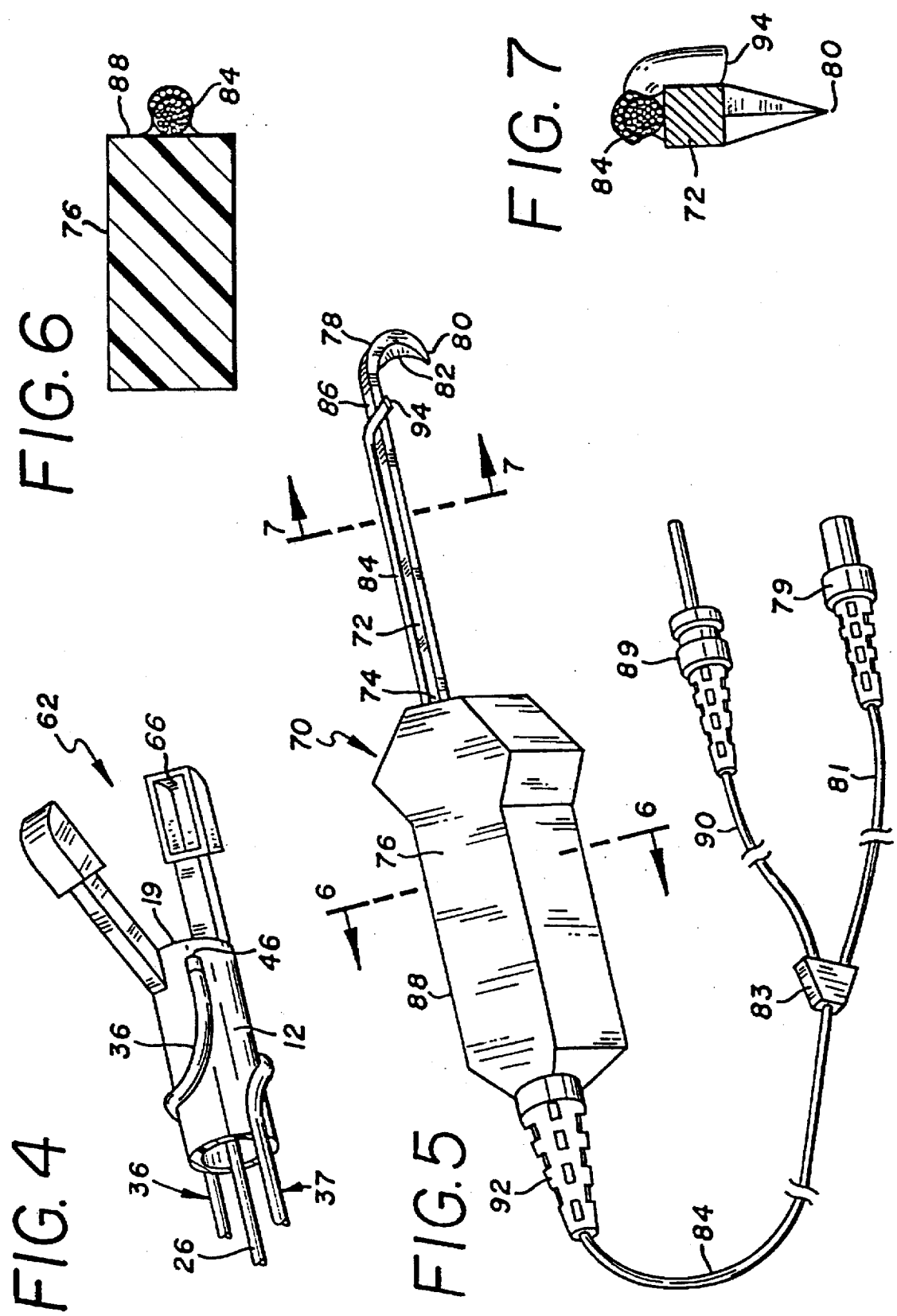

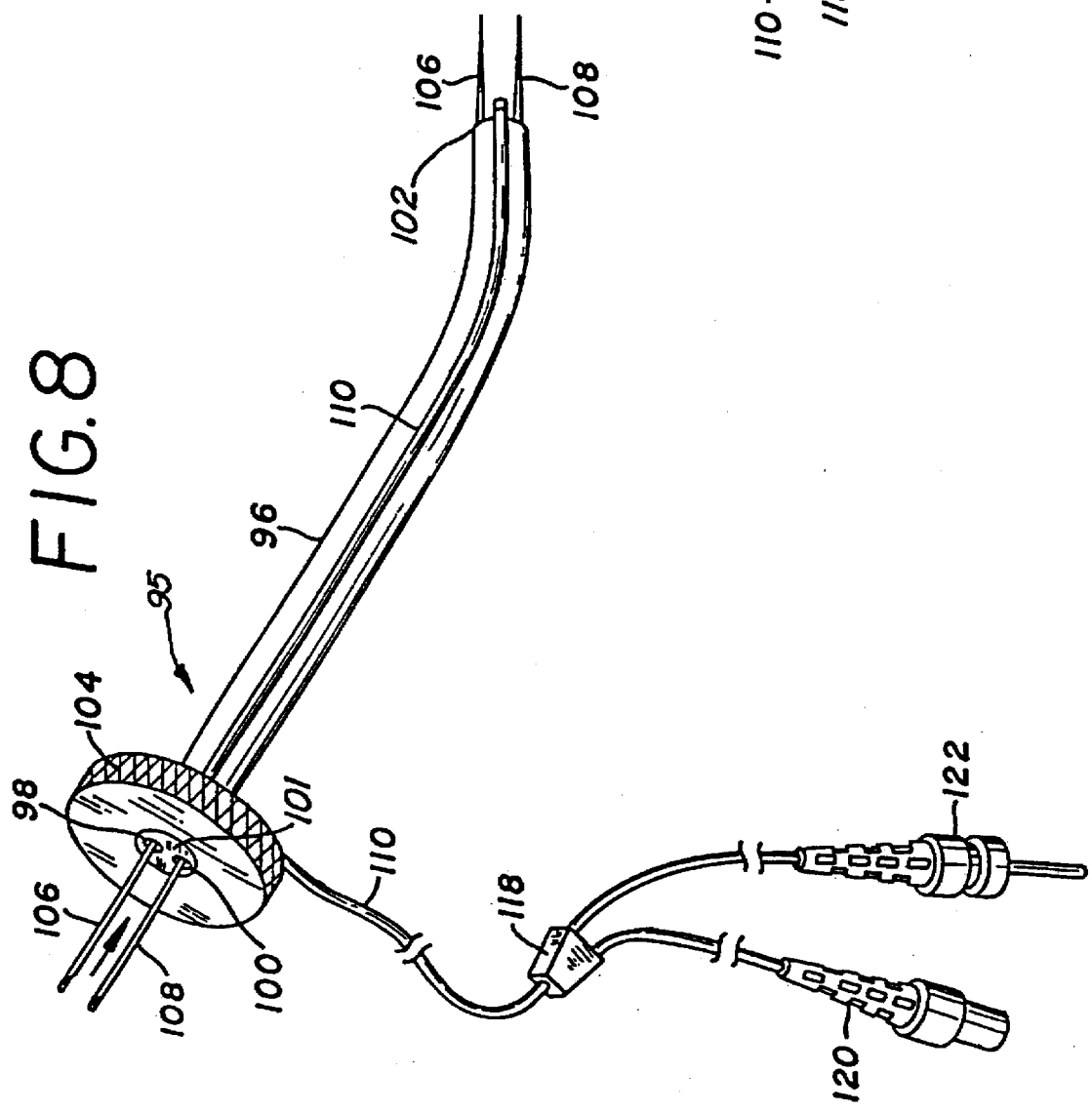

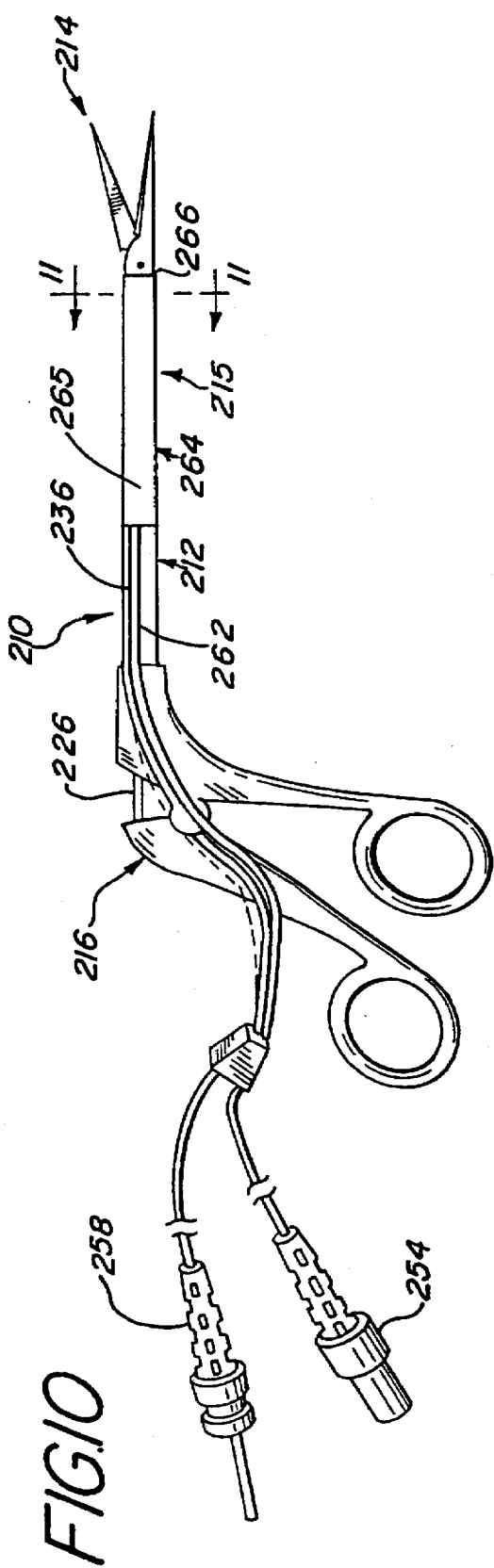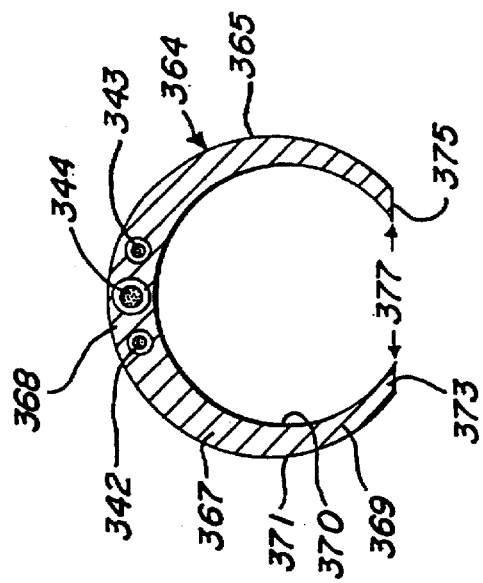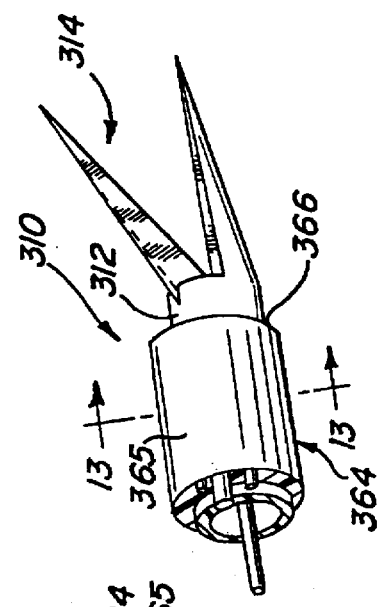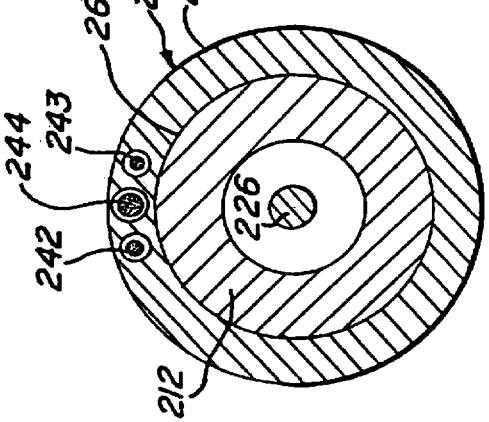

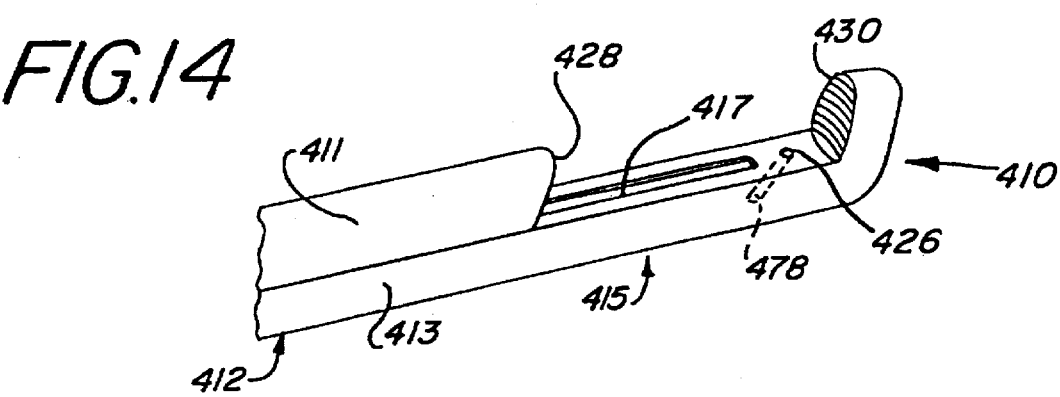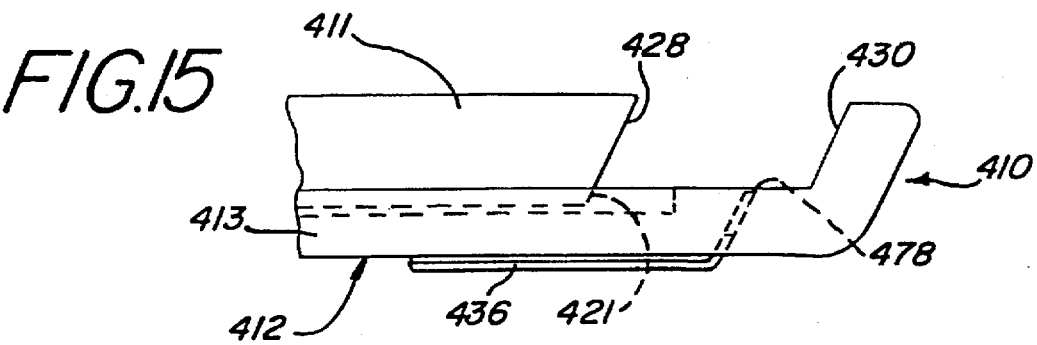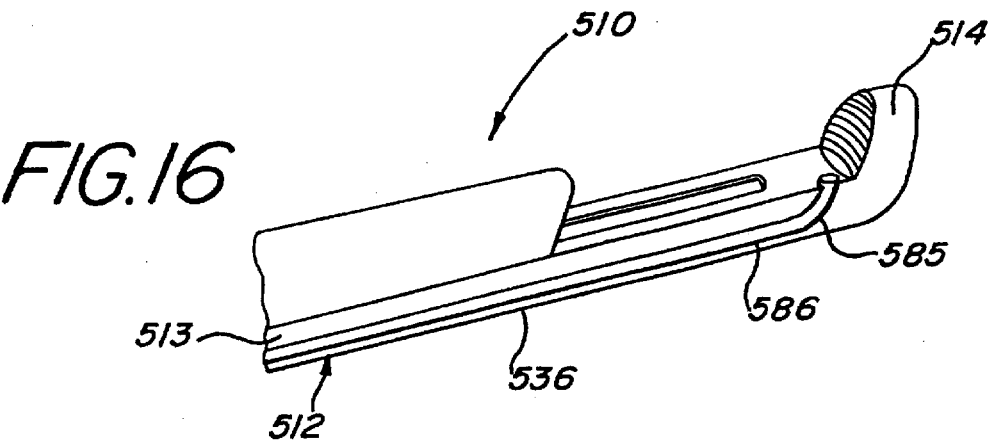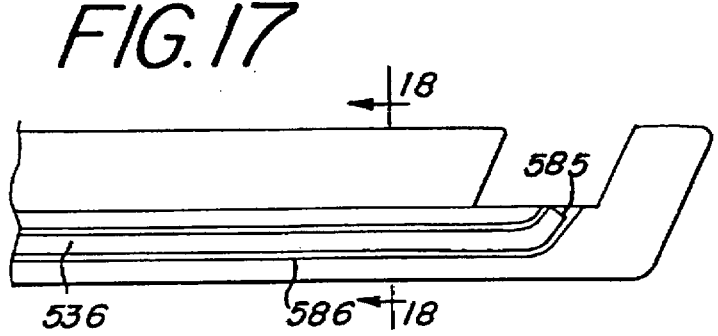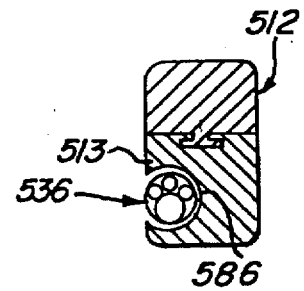

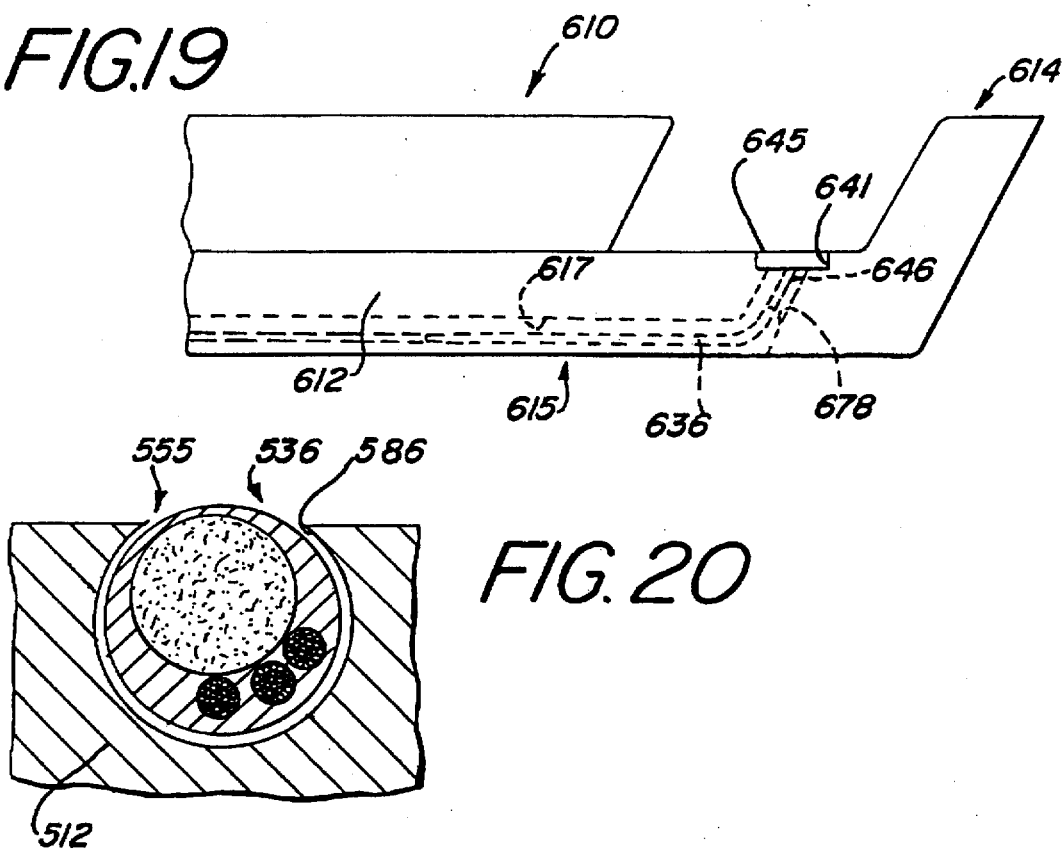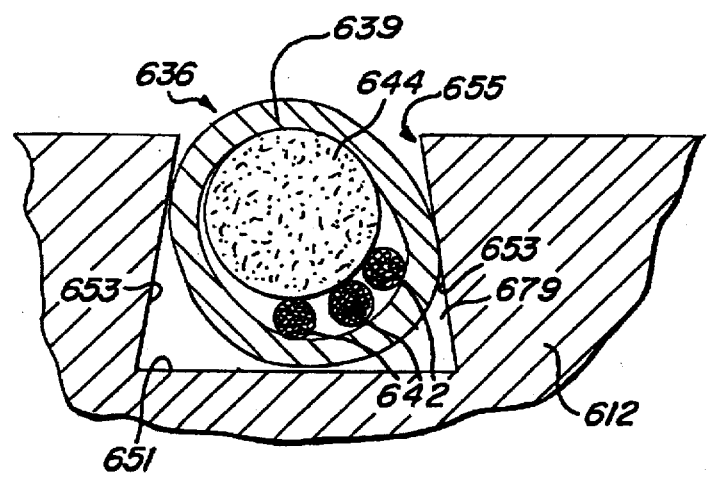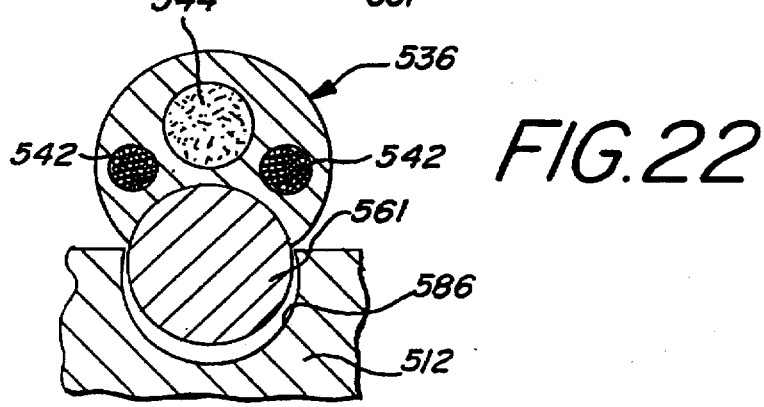

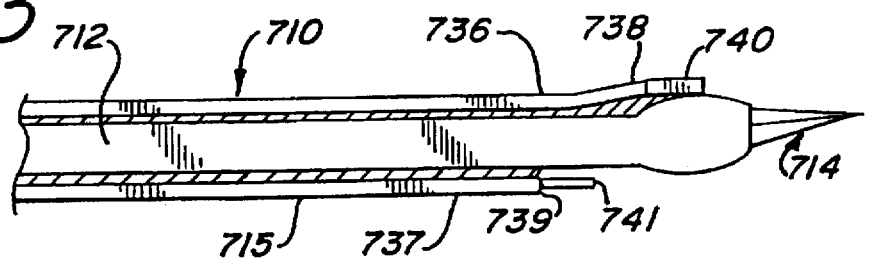
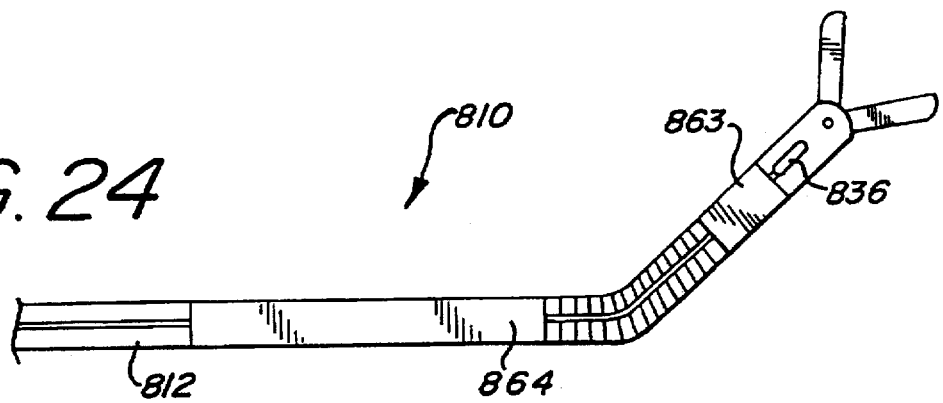
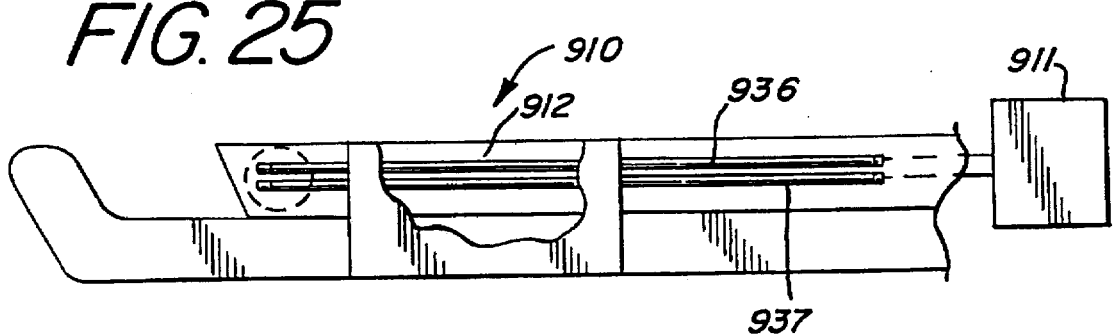
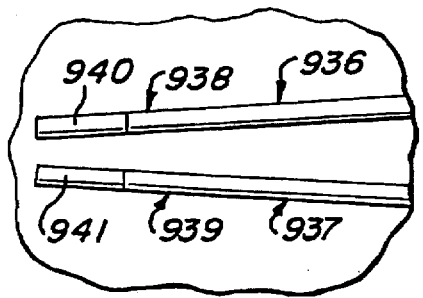

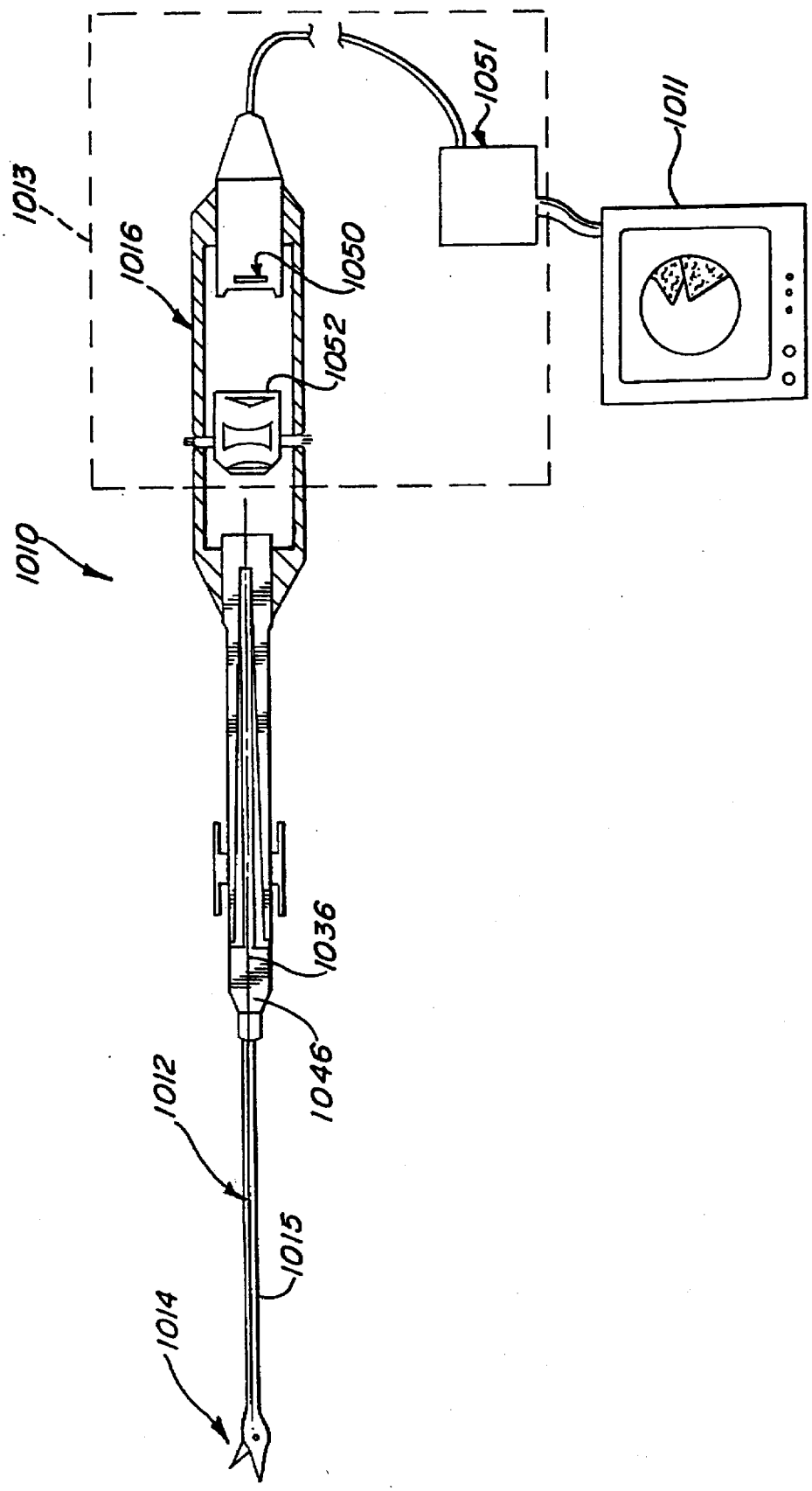

SURGICAL INSTRUMENT AND METHOD FOR USE WITH A VIEWING SYSTEM

This application is a continuation-in-part of international application No. PCT/US92/09616, filed Nov. 6, 1992.

FIELD OF THE INVENTION

This invention relates generally to surgical instruments and more particularly to surgical instruments for improving and facilitating viewing by a surgeon of a surgical site and a working element of the instrument.

BACKGROUND OF THE INVENTION

Many devices and methods utilizing various surgical instruments such as scissors, forceps and the like have been developed over the years for use in surgical operations. Often, the configuration and construction of the surgical instruments have been based on anatomical considerations as well as on the importance of providing a surgeon with tactile information important in achieving proper control over the instrument. Visual aids such as fluoroscopy, x-radiography and fiberoptics are often used, however a surgeon manipulating such an instrument must nevertheless rely on tactile sensitivity to locate, grasp, cut and remove the desired tissue.

Endoscopic instruments have been extensively utilized by surgeons to provide an internal view of an organ, body passage or lumen requiring treatment. Many of these instruments are specially made to include fiberoptic assemblies within their structure. Because of the internal mounting of the fiberoptic assemblies together with flushing and access passageways, such endoscopic instruments tend to be relatively large in diameter, limiting their uses.

Some of these instruments are rigid endoscopes that have a working element or tool located at their distal ends. Such rigid endoscopes provide excellent optical images, but they often suffer from several drawbacks. They require precise alignment and are therefore fairly expensive to manufacture. The optical systems employed do not allow the endoscopes to be bent and this necessarily limits the ability of the surgeon to gain access to many areas of the body to be worked on. Also, a video camera must be clamped onto the proximal end of the endoscope so that the surgeon must hold the camera's weight. This will limit the tactile feel.

One such example is U.S. Pat. No. 5,089,000 to Agee which discloses a surgical instrument for manipulating selected tissue in a body cavity. The Agee device includes a hollow sheath mounted on a complicated handle assembly. The result is a large and bulky instrument with limited tactile feel for the surgeon. Further, the Agee device is straight which limits its access to many areas of the body.

A flexible endoscope, on the other hand, provides access to parts of the body that are not accessible with rigid instruments. The surgeon may pass a flexible tool through a working channel in the endoscope to manipulate tissue at the distal end of the endoscope. With a flexible endoscope, however, it becomes difficult to position the working end, when it is considered that the equal and opposite reaction to a force may easily push the end of a flexible endoscope away from the target tissue.

One attempt to combine flexible and rigid systems is U.S. Pat. No. 4,300,564 to Furihata. The Furihata device uses a relatively large tubular member mounted on the handle of an instrument. The tubular member extends away from the handle of the instrument at an angle and includes a fluid port connected to the tubular member. An endoscope can be inserted in the tubular member but there is no provision for fixing the endoscope such that a predetermined field-of-view for the working end is provided. As will be readily understood, such a design does not provide for good tactile feel particularly when a suction or flushing source is connected to the fluid port.

Another design, such as shown in U.S. Pat. No. 4,759,348 to Cawood uses an externally mounted endoscope on the surgical instrument. Cawood uses an endoscope assembly with a distal optical head equipped with a connector for externally and releasably attaching the head to the neck of a surgical instrument adjacent the distal end of the instrument.

Only the endoscope's optical head is releasably clipped to the distal end of the Cawood surgical instrument. The clip-on head is secured to the surgical instrument just before the surgical procedure in an attempt to make it possible for the surgeon to view the working tip of the instrument. Because of the design, proper alignment and focusing on the working tip of the instrument can be time consuming and frustrating. Because Cawood only connects the endoscope to the distal end of the instrument, there is no provision for the endoscope to have its body follow or conform to the shape of the instrument. Also, the endoscope may come into unwanted contact with surrounding tissue where it is in the body but not attached to the instrument. With such a design, the weight and flexibility of the endoscope can dampen the tactile feel which is so important to a surgeon, and essential to an efficient and successful surgical procedure.

A surgical device whose distal end cannot be precisely maneuvered tends to interrupt a surgeon's tactile feel and ability to control the working element of the instrument and the tissue being manipulated. Moreover, the clip on the Cawood device can provide an obstacle in a surgeon's field-of-view around the endoscope. The size of such an assembly as proposed by Cawood requires a larger than necessary incision to allow entry of the endoscope, the clip, and the surgical tool through the same opening.

In most if not all of these prior instruments, a surgeon's hands are spaced well away from the distal end of the endoscope or instrument which limits the surgeon's precise and accurate control of the distal end of the endoscope or instrument, and the tactile sensitivity. What is needed is a new design which provides an accurate and clear view of the surgical site and the distal operating portion of the surgical instrument. Such a device should also provide for maximizing tactile feedback and sensitivity to locate, grasp, cut and remove the desired tissue. The device should also be small in cross-section to provide for easy access to the tissue and improved tactile feel. The present invention meets these desires.

SUMMARY OF THE INVENTION

The present invention relates to a surgical instrument for use with a viewing system that facilitates surgical procedures and improves the viewing of the surgical site while giving improved tactile feel for the surgeon.

The surgical instrument includes an elongated shaft having a proximal end and a distal end with a handle member mounted on its proximal end for facilitating handling. The shaft also has a distal operating portion extending at least about one-third of the length of the shaft. The distal operating portion is the portion of the shaft which can usually be expected to be inserted into the patient. A working element is disposed on the distal end of the shaft for manipulating tissue during the course of a surgical procedure.

The instrument also includes an elongated optical assembly such as a fiberoptic assembly with image fibers having a proximal end and a distal end with an objective lens mounted on the distal end of the image fibers for defining a field-of-view. The fiberoptic assembly further includes a coupling device at the proximal end of the image fibers for coupling to a viewing system such as an eyepiece. Alternatively, the optical assembly can include a single image fiber in the form of a rod lens, alone or combined with a fiberoptic image bundle. A mounting means provides for mounting the optical assembly to the shaft along substantially the entire length of the distal operating portion with the distal end of the image fibers positioned with a predetermined field-of-view.

In one preferred embodiment, the mounting means includes a bonding agent, such as epoxy, which is used to attach the fiberoptic assembly to the shaft. In a particularly preferred embodiment, the fiberoptic assembly is attached to the exterior of the shaft along substantially the entire length of the shaft and also a portion of the handle member. This allows the fiberoptic assembly to extend from the handle portion to avoid any interference with the grip of the surgeon and thereby give even greater tactile feel. This avoids the problems of prior devices that are either too large or have designs which would interfere with the surgeon's feel when using the instrument.

In another embodiment, the mounting means is a device constructed to be coupled to an exterior surface of the operating portion of the shaft for improved adjustment, and facilitating mounting and removal. The mounting device can also be molded or can be a shrinkable tubing, for example, for a secure compression fitting or shrinkable coupling. The tubing can be heat, water or chemically shrinkable. Shrinkable tubing is particularly adapted for irregularly shaped shafts or flexible shafts. In another alternative embodiment, the mounting means includes a groove, hole or passageway defined by the shaft with a portion of the fiberoptic assembly being received in the groove.

In another preferred embodiment, the mounting means can include a substantially arcuate body having a wall, a distal aperture at one end, a proximal aperture at the other, and an elongated opening or channel between the ends defining a snap-fittable channel. The mounting body is of a sufficient length and diameter to provide a secure connection to the shaft. A portion of the fiberoptic assembly is received within the wall of the arcuate body with at least a portion of the working element being within the field-of-view. Such a mounting body can be unitary, slidably adjustable along an axial axis of the shaft, and can be adhesively bonded to the shaft, if desired.

The fiberoptic assembly can include illumination fibers mounted to the distal operating portion of the shaft for projecting light in the field-of-view. The shaft can also include an actuating mechanism operatively coupled to the working element for appropriate manipulation or cutting of tissue.

The mounting means, shaft and fiberoptic assembly is made sufficiently narrow to minimize the size of a patient's body opening necessary to insert the operating portion therein. It is preferred that this mounting means and fiberoptic assembly combined be less than one-third of the total cross-section area of the instrument at the operating portion. Unlike the prior art devices, a small incision will then be possible. Thus, the present invention goes in a very different direction than the prior art. The prior art seeks complicated structures, which while being versatile, are large and bulky. This means a larger incision, and more importantly, loss of tactile feel for the surgeon.

The fiberoptic assembly can include first and second bundles of image fibers, the bundles being provided with objective lenses on their respective distal ends to provide two different fields-of-view. One field-of-view can provide a close up view while the other provides a wide view. Thus, the objective lenses can have the same or different focal lengths, and the objective lenses can be spaced longitudinally along the shaft. In addition, three dimensional viewing can be possible with this invention.

The present invention also involves a method of retrofitting an existing surgical instrument with fiberoptics. The method starts with an existing surgical instrument including a shaft and a handle, a distal operating portion extending about at least one-third of the length of the shaft and a working element on the distal end of the shaft. A fiberoptic assembly as described above is mounted to at least the distal operating portion of the shaft, such that at least a portion of the working element is within the field-of-view and the tactile feedback of the instrument is substantially unaffected. This allows the surgeon to use an instrument he is familiar with and still have the benefits of fiberoptics.

Some of the advantages of the surgical instrument of the present invention are improved tactile feel, improved viewing of the surgical site and the working element of the instrument, and removably or permanently coupling of the fiberoptic assembly with the surgical instrument. Another advantage is that surgical instruments of the present invention can be bent to gain access to many areas of the body to be worked on where some of the previously mentioned surgical instruments could not access.

Removably coupling the fiberoptics facilitates replacement of fiberoptic assemblies which may be separately sterilized. This is particularly useful because it allows the instrument to be heat sterilized while the fiberoptics are not exposed to heat. In addition, a new set of fiberoptics can be used when one becomes damaged thereby avoiding the cost of replacing the whole instrument.

Numerous other features and advantages of the present invention will become readily apparent from the detailed description of the invention, the accompanying drawings and the appended claims.

BRIEF DESCRIPTION OF THE DRAWINGS

FIG. 1 is a side elevational view of a surgical instrument of the present invention in the form of surgical scissors having a shaft and a scissors as a working element, with an optical assembly mounted to a distal operating portion of the shaft;

FIG. 2 is an enlarged cross-sectional view taken along the plane 2—2 of FIG. 1;

FIG. 3 is an enlarged perspective view of the distal end of the surgical instrument of FIG. 1;

FIG. 4 is a perspective view similar to FIG. 3, but having a fiberoptic assembly mounted on a biopsy forceps;

FIG. 5 is a perspective view of an alternative embodiment of the present invention showing a fiberoptic assembly mounted on a hook knife;

FIG. 6 is a cross-sectional view taken along the plane 6—6 in FIG. 5;

FIG. 7 is a cross-sectional view taken along the plane 7—7 in FIG. 5;

FIG. 8 is an enlarged perspective view of an alternative surgical instrument of the present invention in the form of a surgical stitcher, with a fiberoptic assembly mounted to the shaft of the instrument with a bonding agent;

FIG. 9 is an enlarged view of the distal end of the surgical instrument in FIG. 8;

FIG. 10 is a side elevational view of a surgical instrument similar to that of FIG. 1 showing an alternative mounting means;

FIG. 11 is an enlarged cross-sectional view taken along the plane 11—11 of FIG. 10;

FIG. 12 is an enlarged perspective view of a distal operating portion of an alternative embodiment of a surgical instrument of the present invention, showing a portion of a mounting device mounting a fiberoptic assembly to the shaft;

FIG. 13 is a cross-sectional view of the mounting device of FIG. 12 taken along plane 13—13 of FIG. 12;

FIG. 14 is a partial perspective view of another alternate embodiment of a surgical instrument of the present invention in the form of a Rongeurs having an angled hole through the distal operating portion for receiving at least a portion of a fiberoptic assembly;

FIG. 15 is a partial side elevational view of the surgical instrument of FIG. 14 with a partial view of the fiberoptic assembly;

FIG. 16 is a partial perspective view of a distal operating portion of an alternate embodiment of the surgical instrument of FIG. 14 having a groove along a side external surface of the surgical instrument coupled with a hole for receiving a fiberoptic assembly;

FIG. 17 is a partial side elevational view of the surgical instrument in FIG. 16;

FIG. 18 is an enlarged cross-sectional view taken along the plane 18—18 of FIG. 17;

FIG. 19 is a enlarged partial side elevational view of an alternate embodiment of the surgical instrument in FIG. 14, having a protective window, angled hole and a groove on a bottom exterior surface, adapted for receiving the fiberoptic assembly;

FIGS. 20, 21 and 22 are cross-sectional views of alternative embodiments for the mounting means using grooves;

FIG. 23 is a partial side elevational view of a further surgical instrument in the form of surgical scissors showing two oppositely positioned fiberoptic assemblies mounted to a distal operating portion of the shaft of the instrument, the fiberoptic assembles are laterally offset and adhesively bonded to the shaft;

FIG. 24 is an enlarged partial side elevational view of a further surgical instrument in the form of flexible scissors showing a fiberoptic assembly coupled to a distal operating portion of the instrument;

FIG. 25 is a side elevational view of an embodiment of a surgical instrument in the form of a Rongeurs showing two fiberoptic assemblies;

FIG. 26 is an enlarged partial elevational view of the distal end portion of the fiberoptic assemblies of the surgical instrument of FIG. 25; and FIG. 27 is a side elevational view with an alternative embodiment in a partial cross-sectional view showing a rod lens used as part of the optical assembly.

DESCRIPTION OF THE PREFERRED EMBODIMENTS

As will become apparent to those skilled in the art from a reading of the following description, the present invention may be applied to various types of specialized medical instruments, including cutting and grasping instruments, surgical probes, stitchers, etc. However, the principles will be explained in connection with only a few specific instruments as examples.

Referring to FIGS. 1-3, a surgical instrument of the present invention for use with a viewing system is shown. The surgical instrument 10, includes an elongated shaft 12 with a handle member 16 mounted on a proximal end 18 of the shaft 12 and a distal operating portion 15 extending at least about one-third of the length of the shaft 12. A working element 14 such as scissor blades 28 and 30 is disposed on a distal end 19 of the shaft 12 for manipulating tissue during the course of a surgical procedure. The offset portion of the handle or handle member 16 is the portion of the instrument 10 which is generally held by the surgeon while the distal operating portion 15 is that portion which is generally inserted into or placed such that it can be in contact with the patient. Depending on the design of the instrument, some of the shaft 12 may extend between the handle and the operating portion. In the case of surgical instrument 10, the operating portion 15 is about one-third the length of the shaft 12.

In the device of FIG. 1, the shaft 12 preferably includes an actuating mechanism operably coupled to the working element 14 to operate the element. The shaft 12 can be a rigid tube 40 with its proximal end 18 fitted into a bore formed in a first handle member 20. Pivotally joined to the first handle member 20 at pivot 22 is a second handle member 24. An actuating rod or cable 26 is appropriately affixed to the upper end 25 of the second handle member 24 and extends through the lumen of the tube 40 to join the movable scissor blade 28 of the working element 14. The scissor blade 30 is preferably rigidly secured to the distal end 19 of the tube 40.

As is shown in the cross-sectional view of FIG. 2, the actuating rod or cable 26 passes through the tube 40. Affixed to the exterior wall of the shaft 12 are fiberoptic assemblies 36 and 37.

By grasping the scissors handle members 20 and 24 by their respective finger-receiving loops 32 and 34, and by pivoting the second handle member 24 back and forth relative to the stationary first handle member 20, the rod or cable 26 moves reciprocally within the tube 40 to cause the movable scissor blade 28 to open and close in a scissors-like action relative to the secured scissor blade 30.

The surgical scissors, as thus far described, are conventional. In accordance with the present invention, the surgical instrument also includes at least one optical assembly using at least one image fiber to permit viewing by the surgeon. The optical assembly is preferably fiberoptic assembly 36. Alternatively, a rod lens can be mounted on the operating portion and operably coupled to a flexible fiberoptic bundle having a plurality of image fibers to provide a beneficial configuration of a small optical system on the operating portion of the instrument while still having the benefits of a flexible fiberoptic bundle extending from the handle.

Two elongated fiberoptic assemblies 36 and 37 are shown in FIGS. 1-3. The fiberoptic assemblies 36 and 37 each include image fibers 44 having respective proximal ends 48 and 49, and distal ends, with an objective lens 46 mounted on distal end 38 of the image fibers 44 of fiberoptic assembly 36 for defining a predetermined field-of-view which includes at least part of the working element 14. The distal end of fiberoptic assembly 37 also has mounted an objective lens, but is hidden from the view in FIG. 1. By providing two bundles of image fibers 44 whose objective lenses are focused on the working element 14 of the instrument from two different perspectives, better depth perception and reduced shadowing can be attained.

As can be seen in FIG. 3, the objective lens 46 is affixed to the distal end 38 of the fiberoptic assembly 36 to focus the light rays reflected from the illuminated surgical site onto the plane occupied by the distal end 38 of the image fibers 44 contained within the fiberoptic assembly 36. Fiber optic assembly 37 has the same structure, but is not shown in FIG. 3.

One or both of the fiberoptic assemblies 36 and 37 can include illumination fibers. As shown in FIG. 2, illumination fibers 42 are included as part of the same fiberoptic bundle as the image fibers 44. Alternatively, a single or several illumination fibers can be included separately from the image fibers 44.

The proximal ends 48 and 49 of the fiberoptic assemblies 36 and 37 enter a molded plastic hub member 50 where illumination fibers 42 are separated from the plurality of image fibers and then brought out through a protective sheath 52 to a connector 54 which is adapted to be connected to a light source. Likewise, the plurality of image fibers are brought out through the hub member 50 and through another protective sheath 56 to an appropriate connector 58 which is designed to mate with a viewing system. The viewing system may, in its simplest form, comprise an eyepiece (not shown), which provides direct viewing of the image focused upon the distal end of the image fibers 44 by the objective lens 46. However, the image may also be fed to a video camera whose output is transmitted to a viewing screen for observation by the surgeon and the surgical support staff.

As can best be seen in FIG. 2, mounting means 59 can include a bonding agent 60, such as epoxy, and is provided for mounting the fiberoptic assembly 36 to the shaft 12 along substantially the entire length of the operating portion 15 of the shaft 12. As shown in FIGS. 1–3, the fiberoptic assembly 36 is mounted to the exterior of the operating portion of the shaft 12. The distal end 38 of the image fibers 44 is positioned at a predetermined portion of the working element 14 to define the field-of-view of the fiberoptic assembly 36.

The distal operating portion 15 can extend along various lengths of the shaft 12, but generally extends about one-third or more of the length of the shaft 12. Preferably, the operating portion 15 extends about one-half or more of the length of the shaft 12, and most preferably along substantially the entire length of the shaft 12, to provide secure attachment, flexibility of application, and minimal invasion into a patient's body cavity, while preserving the tactile feedback of the instrument.

As shown in FIGS. 1–3, the mounting means 59, in this case the bonding agent 60, is coupled to an exterior surface 64 of the operating portion 15 of the shaft 12. The mounting means 59 preferably attaches the fiberoptic assemblies 36 and 37 substantially along the entire length of the shaft 12 and a portion of the handle member 16. This provides the best tactile feel for the surgeon because the fiberoptic assemblies 36 and 37 are kept from interfering with the surgeon's hands and the opening in the patient.

Alternatively, the mounting means 59 of this invention can be slidably adjustable, snap-fittable, shrinkably coupled and the like, with respect to the shaft 12, for a secure attachment and coupling. In one embodiment, after use, the fiberoptic assembly 36 can be easily removed to facilitate cleaning and sterilization of the instrument 10 and removal of the optics.

A magnetic coupling technique can be utilized, for example, for initially aligning one or more of the fiberoptic assemblies with the shaft prior to attachment or coupling, or applying an adhesive bonding material and the like. This magnetic coupling technique can be used in any of the surgical instruments of this invention, alone or in combination with one or more of the mounting devices or adhesives.

Only one fiberoptic assembly 36 is necessary to receive the image fibers 44 and illumination fibers 42 in a common sheath. Fiberoptic assemblies suitable for use in practicing the present invention can be of the super-thin type disclosed in U.S. Pat. No. 4,867,529 to Utsumi et al. In one such fiberscope, the outside diameter can be less than about 0.5 mm. The fiberoptic assembly 36 may include about 10,000 image fibers 44, each about 5 to 10 micrometers in diameter, which are fused together at each end to thereby preserve their positional relationship relative to one another.

The viewing system can include appropriate circuitry and means for magnification of the image, to allow a surgeon to see objects that are otherwise difficult to see with the naked eye. An optical system designed for use in the present invention will have a field-of-view defined by a cone whose apex angle, φ (phi), is in the range of from about 50 degrees to about 70 degrees when the object being viewed is in an air environment and a range of about 37 degrees to about 52 degrees if the object is immersed in a saline solution. It will provide a good image of the object placed about 2 mm to about 20 mm from the objective lens 46. A video system used with this optical arrangement will generate an image on a cathode ray television monitor and the diameter of that image will be approximately D=5 in. (127 mm) or greater. The magnification can then be computed using the formula:

$$M=((D/2)/(L\tan\phi/2))$$

where D is the size of the image desired on the CRT screen, L is the distance between the objective lens and the object and φ (phi) is a measure of the wideness of the field-of-view. Using the above formula with the numbers indicated for the various parameters, the magnification, M, to be used is a minimum of about 26 times and a maximum of about 38 times.

The shaft 12 and mounting means 59 can be adapted and constructed to have a small outside diameter such that the instrument 10 can be passed through an introducer, a cannula or directly into a narrow lumen or small surgical incision and still have a sufficient length to allow the working element 14 to reach the organ or tissue to be manipulated or cut.

In one embodiment, the cross-section of the operating portion 15 of the instrument 10 consists essentially of the shaft 12, the image fibers 44, and at least one illumination fiber 42 and the mounting means 59. This provides a surgical instrument of minimum size and maximum tactile feel for the surgeon.

FIG. 4 shows an embodiment similar to the FIG. 1 embodiment except that a fiberoptic assembly is coupled or mounted to a working element 62 that is a conventional Rongeurs forceps. The tubular shaft 12 has cup-shaped jaws or paddles 66 affixed to the distal end 19 thereof and appropriately hinged and connected to an actuating rod or cable 26, similar to that described above. The fiberoptic assemblies 36 and 37 are again routed along substantially the entire length of the shaft 12 with the objective lens 46 arranged along an optical axis so as to be able to view the particular bone or other tissue to be grasped by the forceps' cup-shaped paddles 66 when the scissors-style handle 16 is manipulated.

FIGS. 5-7 illustrate yet another surgical instrument 70 of this invention, in the form of a surgical hook knife, to permit viewing of a nerve, ligament or other tissue to be severed, for example. This instrument 70 includes an elongated rigid shaft 72 having a generally rectangular cross-section as seen in FIG. 6. The shaft 72 has a proximal end 74 fitted into a handle member 76 so that it can be conveniently and comfortably grasped by the surgeon. The shaft 72 is preferably made from stainless steel and its distal end is curved as shown as hook 78, terminating in a point 80 and having a beveled cutting edge or accurate blade 82 extending over the inward-facing arcuate portion of the hook 78.

The instrument 70 is typically used by inserting the shaft 72 of the knife through an opening until the arcuate blade 82 is disposed distally of the tissue to be severed. Cutting takes place by then pulling instrument 70 back in the proximal direction which allows the cutting edge or accurate blade 82 to cut the tissue. Carpal tunnel surgery is often performed using this type of instrument.

At least one fiberoptic assembly is affixed to the instrument 70 in such a way that the surgical site can be viewed, either directly or indirectly, in the manner previously described. Connectors 79 and 89 are adapted to mate with a light source and viewing system, respectively, as previously discussed. The fiberoptic assembly 84 includes illumination and image fibers that pass through sheaths 81 and 90 and terminate in connectors 79 and 89, respectively. The image connector 89 is joined to a plurality of image fibers within the sheath 90 which unite in a hub 83 with the illumination fibers in the fiberoptic bundle 84. This bundle passes through a flexible strain relief member 92 attached to the proximal end of the handle member 76 of the hook knife instrument 70.

As shown in FIGS. 5-7, the fiberoptic assembly 84 extends along an upper side surface 86 of the shaft 72. Upon leaving the shaft 72, the fiberoptic assembly 84 can pass through the handle member 76 or be mounted on a side 88 of the handle member 76 as shown in FIG. 6. Near the distal end of the shaft 72, the fiberoptic assembly 84 wraps about the side surface of the shaft, such that its objective lens 94 becomes optically aligned with the knife cutting edge 82. One observing the image exiting the proximal end of the image fibers in the fiberoptic assembly 84 obtains a clear view of the surgical site where the blade 82 interacts with the tissue. This greatly generally improves a surgeon's ability to locate and identify the tissue to be manipulated or cut.

In the embodiment shown in FIGS. 5-7, the fiberoptic assembly 84 is preferably mounted by epoxy bonding along substantially the length of the exterior surface of the shaft 72. As shown, the fiberoptic assembly 84 can be mounted on one surface such as the upper side surface 86 and wrapped around the shaft 72 to provide a side view. This is advantageous where space is available on one side for the fiberoptic bundle but viewing is desired from another angle. A similar wrap around function is shown in FIGS. 1 and 4.

FIGS. 8 and 9 show another surgical instrument of the present invention in the form of a surgical stitcher, such as an ACCUFEX® brand Meniscal Stitcher sold by Accufex Microsurgical, Inc. used in arthroscopic knee surgery. The surgical instrument 95 has an elongated rigid tubular shaft 96 having lumens 98 and 100 extending from its proximal end 101 to its distal end 102. Surrounding the proximal end 101 of the shaft 96 is a knurled outwardly extending handle member 104. The lumens 98 and 100 accommodate stitching needles 106 and 108.

Mounted on the exterior of the shaft 96 is an optical fiber assembly 110 including illumination fibers or bundle 114 and image fibers or bundle 116 as best seen in FIG. 9. Attached to the distal ends of the image fibers 116 is an objective lens 115 positioned to view the distal end portions of the needles 106 and 108 exiting the lumens 98 and 100 in the shaft 96.

The illumination fibers 114 are brought out through a hub member 118 to a connector 120 adapted to mate with a jack of a suitable light source (not shown). Similarly, the image fibers 116 pass through the hub member 118 and terminate in a connector 122 adapted to mate with the image input of a suitable viewing device, such as a video camera and associated video display means.

In use, the rigid tubular shaft 96 acts as an introduction cannula and it is passed through a small surgical opening into a knee joint space so that its distal end 102 can be brought up against the meniscus at a desired location. By viewing the image through the fiber optic assembly 110, a surgeon is able to precisely locate the distal end 102 of the instrument 95 at the desired site. The instrument 95 is oriented so that the needles 106 and 108, having been inserted in the entire length of the shaft 96, will pierce both sides of the tear in the meniscus to be repaired, and will continue on through the capsule and soft tissues until the needles 106 and 108 perforate and exit the skin opposite the small surgical entry. The needles 106 and 108, with a long strand of suture material passing through their eyes, are then pulled out of the tissue, and a loop of suture material is drawn taut so as to complete the internal half of the stitch. A knot is then tied and drawn tight against the outer surface of the capsule through a small incision bridging the exit perforations of the needles 106 and 108. This procedure may be repeated as many times as necessary to effect repair of the tear.

The advantages of the present invention can be appreciated upon considering a typical arthroscopic surgical procedure. In conventional arthroscopic surgery, it is necessary to make a plurality of punctures through the skin and into the capsule of a joint. Through this plurality of percutaneous punctures, also called "operating portals", tools are passed. One tool commonly used is a meniscus cutter. In conventional prior art arthroscopic surgical procedures, the action of a meniscus cutter is observed with a separate arthroscope passed through a second operating portal different from the one accommodating the meniscus cutter. One or more of a second type of percutaneous punctures, called "irrigation portals", may also be made through the skin and into the joint capsule. Irrigation fluid, which distends the joint and sweeps away blood clouded fluid, may be injected through and removed from the irrigation portals. While irrigation portals are generally of a small diameter, operating portals must necessarily be large enough to pass surgical tools and arthroscopes. It is, of course, desired to limit the number and size of operating portals required for surgery.

By using the instrument of the present invention, it is no longer necessary to use a separate rigid arthroscope and its separate incision. The viewing optics of the present invention can be adhered or appropriately mounted to a portion of an exterior surface of the meniscus cutter, thus obviating the need for a relatively large operating portal which would otherwise be used to accommodate that arthroscope.

FIG. 10 shows an alternative embodiment 210 similar to FIG. 1. In this embodiment, the mounting means is a mounting device 264, substantially complementarily configured to receive at least a portion of a shaft 212, for a minimal invasive diameter and secure attachment. The handle member 216, actuating means 226 and connectors 254 and 258 are as described before. As shown in FIG. 11, the mounting device 264 includes a circular cross-section and is substantially tubular in shape. It should be noted that various shapes, geometries and cross-sections can be used in this invention. The mounting device 264 can be made of a molded or shrinkable tubing 265. In one embodiment, the mounting device 264 is in the form of a tube with a thin wall retaining the fiberoptic assembly 236 between the wall of the tube and the shaft 212 having at least one conduit for receiving the image fibers 244. This provides a tight and conforming fit. When used this way, the fiberoptic assembly 236 can first be attached to the shaft 212 magnetically or by use of an adhesive. The mounting device 264, such as a shrinkable tubing 265, is then placed over the combination of the fiberoptic assembly 236 and shaft 212 to retain the fiberoptic assembly 236 in place. Where the working element 214 is larger in size than the shaft 212, shrinkable tubing 265 is particularly useful. Instead of placing the fiberoptic assembly 236 between the shrinkable tubing 265 and shaft 212, it can be placed within the wall of the shrinkable tubing 265.

As shown in FIG. 11, the molded or shrinkable tubing 265 alternatively can include three conduits for receiving the image fibers 244, and first and second illumination fibers 242 and 243. The illumination fibers 242 and 243 are mounted to an operating portion 215 of the shaft 212 with the distal end of the illumination fibers 242 and 243 positioned to project light in the field-of-view which includes the working element 214. As best shown in FIG. 11, the cross-section area of the mounting device 264, the image fibers 244 and illumination fibers 242 and 243 combined is less than about one-third of the cross-section area of the total cross-section area defined by the operating portion 215 of the shaft 212, the mounting device 264, the image fibers 244 and illumination fibers 242 and 243.

A bonding agent 261 can also be used to couple an exterior surface of the shaft 212 to an interior surface of the tubing 265. A further bonding agent 262 can also be utilized to couple the fiberoptic assembly 236 to the shaft 212 where it extends beyond the mounting device 264. As before, a portion of the fiberoptic assembly 236 can also be mounted on the handle member 216. In FIG. 10, the fiberoptic assembly 236 is shown flush with the distal end 266 of the mounting device 264, thus further bonding is not necessary near the working element 214.

As shown in FIG. 10, the operating portion 215 of the shaft 212, that portion which can be expected to be inserted into the patient, extends over half of the length of the shaft 212. This portion of the shaft 212 is therefore covered by the mounting device 264. As can be seen in the embodiment of FIG. 10, the mounting means includes the tubing 265 and bonding agent 262 to give particularly effective mounting. However, the bonding agent 262 is not necessary and the tubing 265 can function as the mounting means, and if desired, can extend further along the shaft 212.

Suitable materials for the mounting device 264 include heat-shrink teflon, polyolefin and other heat-shrink plastics shown in the art.

As a still further alternative for the mounting means, a clip mounting device 364 for use with a surgical instrument 310 of this invention, is shown in FIGS. 12 and 13. The surgical instrument 310 of FIGS. 12 and 13, is similar in structure to that of FIGS. 10 and 11 with the mounting means being the mounting device 364. FIG. 12 is a cut-away view and the mounting device 364 extends a length along the shaft 312 similar to that shown for the mounting device 264 in FIG. 10.

The mounting device 364 comprises a substantially arcuate body 365 having a thin wall 367 defining an upper section 368 and a lower section 369, inner and outer surfaces 370 and 371, a distal aperture at a distal end 366, a proximal aperture at a proximal end (not shown) and an axial channel between the ends. The arcuate body 365 has an elongated opening or channel deferred between the ends 373 and 375 defining a snap-fittable channel 377 for receiving a portion of the shaft 312. The mounting device 364 is of a sufficient length and diameter to provide a secure connection to the shaft 312. A portion of the fiberoptic assembly is received within the thin wall 367 of the arcuate body 365 to place at least a portion of the working element 314 within the field-of-view. The mounting device 364 is coupled to the distal operating portion of the shaft 312. It should be noted that the mounting device 364 can also be utilized to securely couple other portions of the fiberoptic assembly to other locations along the shaft 312 as well.

As shown in FIGS. 12 and 13, the fiberoptic assembly is carried within the upper section 368. More particularly, conduits receive image fibers 344, and first and second illumination fibers 342 and 343, respectively. Where desired, the mounting device 364 can be slidably adjusted along the shaft 312. The inner surface 370 of the mounting device 364 can be adhesively bonded with a bonding agent to an instrument for minimizing unwanted movement or slippage. Alternatively, the resiliency of its arcuate body 365 will retain the mounting device 364 on the shaft 312. Suitable materials for the arcuate body 365 include polypropylene, teflon, and other plastics known in the art.

Exterior mounting of the fiberoptics by use of the mounting devices and methods of this invention provide for simplified manufacture and repair of instruments, facilitate attachment and removal of the components, and do not require complicated tooling such as drilling or milling to manufacture.

FIGS. 14 and 15 show an alternate surgical instrument of the present invention. The surgical instrument 410 includes an elongated shaft 412 having a proximal portion mounted on a handle (not shown) and a distal operating portion 415 defining an opening 478. A working element in the form of a stationary element 430 and moving element 428 is disposed on the distal operating portion 415 of the shaft 412. The opening 478 is proximate to the working element, in this case moving element 428. An elongated, flexible fiberoptic assembly 436 is mounted on the shaft 412. The assembly 436 includes illumination and image fibers in a common sheath with an objective lens 426 affixed to the distal end of the image fibers, for defining a predetermined field-of-view.

In FIGS. 14 and 15, the fiberoptic assembly 436 is mounted on the shaft 412 with a portion extending at least partially through the opening 478, such that at least a portion of the working element is within the field-of-view when in use. The opening 478 is preferably a hole which extends through the shaft 412 with the fiberoptic assembly 436 extending at least partially through the hole.

First and second elements 411 and 413 comprising the shaft 412 are complementarily configured and include an elongated groove 417 and flange 421 for allowing lateral movement and interconnection. The fiberoptic assembly 436 is appropriately coupled or adhesively bonded to the shaft 412 at least adjacent to the distal operating portion 415 or along the entire length of the shaft 412. As shown, the fiberoptic assembly 436 is mounted on the exterior of the shaft 412 along its length toward the handle (not shown). Alternatively, the bottom of the shaft 412 can define a groove into which the fiberoptic assembly 436 is received. The fiberoptic assembly 436 is also preferably bonded within the opening 478.

An alternative embodiment for a Rongeurs forceps 510 is shown in FIGS. 16–18. The mounting means includes an arcuate and inclined opening or groove 585 that extends from adjacent the working element 514 along the side portion 513 of the shaft 512. A side groove 586 on the exterior surface of side portion 513 of the shaft 512 is associated with the arcuate groove 585 and extends from the arcuate groove 585 in a direction toward the proximal handle member (not shown). The side groove 586 extends along the axis of the shaft 512 and is adapted to receive at least a portion of the length of the fiberoptic assembly 536. The arcuate groove 585 is constructed to give an advantageous view and perspective of the working element 514. If desired, an adhesive can be utilized to bond the fiberoptic assembly 536 to the grooves 585 and 586 for an improved and secure coupling. It should be noted, however, that an adhesive is not necessary in this embodiment. The resiliency of the fiberoptic assembly 536 can be used to retain itself in the grooves 585 and 586. In the case where an adhesive is used, the adhesive need not be permanent to allow the components to be disconnected, removed, cleaned and the like.

An alternative embodiment for a mounting means on a Rongeurs forceps 610 is shown in FIG. 19. The shaft 612 defines an opening, in this case a hole 678 which extends through shaft 612. Associated with the hole 678 is a groove 617 defined by the bottom portion of the shaft 612 to receive and hold the fiberoptic assembly 636. The benefit of this arrangement is that a fiberoptic system is added to the instrument 610 without increasing the cross-section of its operating portion 615. This is a particularly useful design for retro-fitting existing instruments. Shaft 612 defines a substantially circular recess 641 for receiving a protective window 645, for minimizing damage to the objective lens 646 of the fiberoptic assembly 636. The protective window 645 is preferably positioned adjacent the objective lens 646 and is flush with the exterior surface of the shaft 612.

The protective window 645 can be any transparent or clear material that can withstand the environment to which it will be exposed to. The materials for the window 645 can include glass, epoxy, sapphire, various plastics and the like.

FIGS. 20, 21 and 22 show various embodiments for mounting means using grooves such as shown in FIGS. 16–19. These designs can be used with adhesives or bonding agents, but are generally not used with such so that the fiberoptic assemblies are releasably retained in the grooves.

As shown in FIG. 20, the side groove 586 is circular and complementarily configured to receive the fiberoptic assembly 536 securely on the shaft 512. The circular groove 586 as shown in FIG. 20 can have a slightly larger diameter than the outer diameter of the fiberoptic assembly 536 for a tight and secure fit, without compressing the fiberoptic assembly 536. As can be seen, the top opening 555 of the side groove 586 defined by the shaft 512 is smaller across than the maximum diameter of the side groove 586 and the diameter of the fiberoptic assembly 536. This allows the resiliency of the fiberoptic assembly 536 to provide a snap fit.

In FIG. 21, a groove 679 is shown which is substantially trapezoidal in shape, having a planar bottom 651 and sidewalls 653. The sidewalls 653 are angled inwardly travelling radially away from the bottom 651 toward the top opening 655 to compress and securely hold the fiberoptic assembly 636 in the shaft 612. The fiberoptic assembly 636 can be provided with an elongated resilient case 639 into which the image fibers 644 and illumination fibers 642 (in this case 3) are received. The case which can be made of a plastic or rubber tubing known in the art allows the fiberoptic assembly 636 to be snapped in and out of the groove 679. Alternatively, the case 639 can be made of metal such as stainless steel and be pre-bent to fit into the groove 617 and hole 678 (FIG. 19) or in the case of a device as in FIGS. 16–18, into the side arcuate groove 585 to provide the desired view.

Still another alternative mounting means is shown in FIG. 22. A cross-sectional view of a portion of a surgical instrument is shown, having a semi-circular side groove 586 defined by the shaft 512. The fiberoptic assembly 536 includes an elongated retaining member 561 in the form of an elastic member, substantially along the length of the fiberoptic assembly 536, adapted to be received in the groove 586. The retaining mounting member 561 is complementarily configured to be tightly received in groove 586, to allow the fiberoptic assembly 536 to be removably coupled to the shaft 512. The fiberoptic assembly 536 in FIG. 22 includes image fibers 544 with illumination fibers, or optionally, two illumination fibers 542.

The retaining member 561 can be made of a resilient material such as plastic, rubber, or flexible magnetic material for various applications, so long as the material can withstand the environment to which it will be exposed to and will interconnect and mate with the groove 586.

As shown in the figures, the fiberoptic assembly can be releasably received in the grooves, and easily removed, for example, for sterilization of the surgical instrument and replacement of the fiberoptic assembly.

Another embodiment of the surgical instrument 710 of this invention is shown in FIG. 23. The surgical instrument 710 is in the form of a scissors and includes an elongated shaft 712 having a proximal handle as described before and a distal operating portion 715. A working element 714 in the form of scissors is disposed on a distal end of the shaft 712 for manipulating or cutting tissue. Also provided are two elongated fiberoptic assemblies 736 and 737 each having distal ends 738 and 739 with lenses 740 and 741 mounted on respective distal ends 230 and 232 for defining different predetermined first and second field-of-views respectively.

This construction with at least two fiberoptic assemblies 736 and 737 can provide two different perspectives of the working element 714, improved depth perception, reduced shadowing and alternate views of the surgical site. The distal ends 738 and 739 of the fiberoptic assemblies 736 and 737 are laterally offset to provide a close-up and wide field-of-views, respectively. In lieu of laterally offsetting the assemblies 736 and 737, the distal ends 738 and 739, and the lenses 740 and 741 can have different focal lengths for providing a close-up and wide field-of-view, for example.

A surgeon can utilize a switching system to switch back and forth as desired for close-up or wide views, when observing the field-of-views, for example. The two views can be observed simultaneously on a single monitor, or switching means can be used to allow simultaneous or alternative observation of the field-of-views, for example.

In FIG. 24, a further alternate embodiment of the surgical instrument is shown, in the form of flexible forceps. This surgical instrument 810 includes mounting means preferably on those portions of the instrument 810 which do not flex. As shown, mounting devices 863 and 864 can be molded or shrunk to respective portions of the shaft 812 to retain the fiberoptic assembly 836. The mounting devices 863 and 864 can include the features described with respect to the mounting devices in the previous figures. Alternatively, a bonding agent can be used as described above. The mounting devices 863 and 864, and fiberoptic assembly 836 can be flexible to allow the fiberoptic assembly 836 to be adjusted with the instrument 810, without interrupting or misaligning the field-of-view.

An alternate embodiment of the present invention is shown in FIGS. 25 and 26. The structure in this embodiment is similar to many of the embodiments previously discussed. The surgical instrument 910 includes elongated fiberoptic assemblies 936 and 937 having distal ends 938 and 939 defining a first and a second predetermined field-of-views. The distal ends 938 and 939 have objective lenses 940 and 941 having substantially similar focal lengths.

The distal ends 938 and 939 are slightly angled toward each other, as shown in FIG. 26, for example, providing a stereoscopic image. The viewing system 911 provides a stereoscopic image defined by the first and second fields-of-view for real time or concurrent viewing of the surgical site. If two eyepieces are used in a binocular-like fashion, for example, each field-of-view can be fed separately and concurrently to each eyepiece. Alternatively, each field-of-view can be fed to one or more separate monitoring devices for viewing the surgical site. In one embodiment, the viewing system 911 includes a device for providing a three-dimensional image defined by the fields-of-view.

The present invention includes a method of retrofitting an existing surgical instrument to carry fiberoptics. This can be done with the examples of FIGS. 1–7 by using a bonding agent as described above. To help align the distal end of the fiberoptic assembly to provide a proper field-of-view, a reference gauge can be used. The reference gauge includes at least two steps, one for the end of the instrument and one for the distal end of the fiberoptic bundle to locate the lens while the fiberoptic bundle is being mounted to the shaft. In the case of an instrument such as in FIGS. 14 and 15, the opening 478 is drilled in the distal operating portion 415 adjacent the stationary element 430. The fiberoptic assembly 436 is then inserted into the opening 478 and an appropriate bonding agent is used to fasten it to the shaft 412.

In the example of FIGS. 16–18, a portion of the shaft 512 is milled to provide the grooves 585 and 586 which extend on the outer surface of the shaft 512. Thereafter, the fiberoptic assembly 536 is mounted in the grooves 585 and 586 as discussed above.

In the case of the embodiment in FIG. 19, the hole 678 is drilled in an existing surgical instrument adjacent a working element 614. The shaft 612 is then appropriately milled to create a groove like that shown in FIGS. 20–22 to receive the fiberoptic assembly 636.

Referring to FIG. 27, a still further alternate surgical instrument 1010 of this invention is shown in the form of a scissors. The surgical instrument 1010 is adapted for use with a viewing system 1011. The surgical instrument 1010 includes an elongated shaft 1012 including a working element 1014 on a distal operating portion 1015, and a handle 1016. The optical assembly 1036 uses an image fiber in the form of a rod lens 1046. The rod lens 1046 is mounted on at least an exterior portion of the shaft 1012. Also provided is an intermediate device 1013 between the rod lens 1046 and viewing system 1011 for transferring an image from the rod lens 1046 to the viewing system 1011.

In one embodiment, the intermediate device 1013 includes a charge coupled device (CCD) chip 1050 and a camera 1051, coupled between the rod lens 1046 and the viewing system 1011. The CCD chip 1050 is substantially adjacent to and preferably enclosed in the handle 1016. The intermediate device 1013 can further include focusing lens system 1052 in the form of a focusing ring, for example, for focusing the image from the rod lens 1046. The proximal portion of the rod lens 1046, the focusing lens system 1052 and the CCD chip 1050 are substantially enclosed and aligned in the handle 1016.

Although not shown in FIG. 27, the intermediate device 1013 can include a flexible fiberoptic viewing bundle as detailed with respect to the surgical instruments of this invention. The fiberoptic bundle would be operatively associated with the proximal end of the rod lens 1046 and the viewing system.

It should be apparent to those skilled in the art that by appending the optical assemblies to the shafts along the distal operating portion extending at least about one-third of the length of the shaft or about one-half the length, or substantially the entire length of the shaft, the surgeon will still receive the desirable tactile response from the instrument. Also, improved balance and tactile feel can be achieved. Because the fiberoptic assemblies, and mounting devices of the instant invention are made to conform to the profile of the instrument, such instruments can be passed through a very small incision or through the lumen of a cannula or introducer, which is a significant advantage over many prior art arrangements and devices.

Although the present invention has been described with reference to certain preferred embodiments, numerous modifications and variations can be made by those skilled in the art without departing from the novel spirit and scope of this invention.

What is claimed is:

1. A surgical instrument for use with a viewing system, comprising:
   (a) an elongated shaft having a proximal end, a distal end and a distal operating portion;
   (b) a handle member having a portion offset from the shaft and mounted on the proximal end of the shaft, the offset portion of the handle member adapted to be held by a user of the instrument;
   (c) a working element disposed on the distal end of the shaft for manipulating tissue during the course of the surgical procedure;
   (d) an elongated optical assembly including an image fiber having a proximal end and a distal end with an objective lens mounted on the distal end of the image fiber for defining a predetermined field-of-view, the assembly including coupling means associated with the proximal end of the image fiber for operably coupling the image fiber to the viewing system; and
   (e) mounting means for mounting the optical assembly to the shaft and the offset portion of the handle member with the distal end of the image fiber positioned with a predetermined portion of the working element within the field-of-view of the optical assembly, the assembly extending along substantially the entire length of the shaft and onto the offset portion of the handle member to be coupled to the viewing system.

2. The surgical instrument of claim 1 wherein the mounting means is coupled to the exterior of the shaft.

3. The surgical instrument of claim 1 wherein the optical assembly is also mounted on and extends from a proximal portion of the handle member.

4. The surgical instrument of claim 1 wherein the optical assembly further includes a rod lens mounted on the operating portion of the shaft.

5. The surgical instrument of claim 1 wherein the mounting means is substantially complementarily configured to receive at least the operating portion of the shaft.

6. The surgical instrument of claim 1 wherein the mounting means comprises a molded or a shrinkable tubing.

7. The surgical instrument of claim 1 further comprising an illumination fiber mounted to the operating portion of the shaft having a distal end positioned to project light in the field-of-view.

8. The surgical instrument of claim 1 wherein the cross-section area of the mounting means and optical assembly is less than about one-third of the cross-section area of the combined cross-section area of the operating portion of the shaft, the mounting means and the optical assembly.

9. The surgical instrument of claim 8 wherein the optical assembly includes an illumination fiber.

10. The surgical instrument of claim 1 wherein the cross-section of the instrument at the operating portion of the shaft consists essentially of the shaft, a plurality of image fibers, an illumination fiber and the mounting means.

11. The surgical instrument of claim 1 wherein the shaft includes actuating means operatively coupled to the working element.

12. The surgical instrument of claim 1 wherein the mounting means includes a tube.

13. The surgical instrument of claim 1 wherein the mounting means includes a groove defined by the shaft with a portion of the optical assembly being received in the groove.

14. The surgical instrument of claim 13 wherein the groove has a top opening and a bottom, the bottom being wider than the top opening.

15. The surgical instrument of claim 14 wherein at least a portion of the optical assembly is releasably received in the groove.

16. The surgical instrument of claim 14 wherein the optical assembly includes an elongated retaining member, the retaining member being received in the groove.

17. The surgical instrument of claim 1 wherein the mounting means includes a hole defined by the operating portion of the shaft proximal to the working element with a portion of the optical assembly extending at least partially through the hole.

18. The surgical instrument of claim 17 wherein a further portion of the optical assembly is mounted along the exterior of the shaft.

19. The surgical instrument of claim 1 wherein the optical assembly further comprises a second image fiber, the two image fibers being provided with an objective lens on their respective distal ends to provide two fields-of-view.

20. The surgical instrument of claim 19 wherein the first and second image fibers are connected to a single coupling means to simultaneously provide the fields-of-view to the viewing system.

21. The surgical instrument of claim 19 wherein the objective lenses have different focal lengths.

22. The surgical instrument of claim 19 wherein the objective lenses are spaced longitudinally along the shaft.

23. The surgical instrument of claim 1 wherein the mounting means includes a groove defined by the shaft with a portion of the optical assembly being removably receivable in the groove.

24. The surgical instrument of claim 1 wherein the optical assembly is removably mounted to at least the shaft.

25. A surgical instrument for use with a viewing system, comprising:
(a) an elongated shaft having a handle on its proximal end, a proximal portion, a distal operating portion and including actuating means for manipulating tissue during the course of a surgical procedure, the distal operating portion being displaceable to alternative positions wherein the distal operating portion does not have the same axis as the proximal portion of the shaft;
(b) a working element on the distal portion of the shaft and operably associated with the actuating means for manipulating tissue during the course of a surgical procedure;
(c) an elongated flexible fiberoptic assembly mounted along the length of the shaft and extending from the handle, the assembly including a bundle of image fibers having a proximal end and a distal end with an objective lens mounted on the distal end of the image fibers for defining a predetermined field-of-view with at least a portion of the working element; and
(d) coupling means at the proximal end of the image fibers for coupling to the viewing system.

26. The surgical instrument of claim 25 wherein the fiberoptic assembly is at least partially received in the shaft.

27. The surgical instrument of claim 25 wherein the fiberoptic assembly is removably mounted on the shaft.

28. The surgical instrument of claim 25 wherein the fiberoptic assembly further comprises an illumination fiber.

29. The surgical instrument of claim 25 wherein the cross-section of the instrument at the operating portion of the shaft consists essentially of the shaft, the image fibers, and an illumination fiber.

30. A method of retro-fitting a surgical instrument with fiberoptics, comprising the steps of:
(a) starting with an existing instrument including a shaft having a handle with an offset portion and a distal operating portion extending at least about one-third of the length of the shaft and a working element on the distal operating portion;
(b) providing a fiberoptic assembly having image fibers with an objective lens mounted on the end of the image fibers and defining a field-of-view;
(c) mounting a tube to the shaft; and
(d) removably mounting a fiberoptic assembly to the shaft by the tube and onto the offset portion of the handle so that the fiberoptic assembly extends along substantially the entire length of the shaft, such that at least a portion of the working element is within the field-of-view and the tactile feedback of the surgical instrument is substantially unaffected.

31. The method of claim 30 wherein the mounting step includes applying a bonding agent to attach the fiberoptic assembly to the shaft.

32. A method of retro-fitting a surgical instrument with fiberoptics, comprising the steps of:
(a) starting with an existing surgical instrument including a shaft having a distal operating portion extending at least about one-third of the length of the shaft and a working element on the distal operating portion;
(b) providing a fiberoptic assembly having image fibers with an objective lens mounted on the end of the image fibers and defining a field-of-view; and
(c) mounting the fiberoptic assembly to at least the distal operating portion of the shaft using a reference gauge to align the objective lens of the fiberoptic assembly with the working element, such that at least a portion of the working element is within the field-of-view and the tactile feedback of the surgical instrument is substantially unaffected.

33. The method of claim 32 wherein the mounting step includes:
(a) inserting at least the operating portion of the shaft and a portion of the fiberoptic assembly into a length of shrinkable tubing; and
(b) shrinking the tubing to substantially couple the operating portion of the shaft with the fiberoptic assembly within and along the shrinkable tubing.

34. The method of claim 32 wherein the mounting step includes cutting a groove in at least a portion of the shaft and positioning a portion of the fiberoptic assembly in the groove.

35. The method of claim 34 wherein the fiberoptic assembly is releasably received in the groove.

36. The method of claim 32 wherein the mounting step includes fitting a mounting device, comprising a substantially tubular body having a distal aperture at one end, a proximal aperture at the other, and an axial channel between the ends, to the operating portion of the surgical instrument.

37. The method of claim 36 wherein the fitting step includes slidably adjusting the mounting device with respect to the operating portion of the surgical instrument.

38. A method of retrofitting a surgical instrument to carry fiberoptics, comprising the steps of:
   (a) starting with an existing surgical instrument including a shaft having a distal operating portion and a working element mounted on the distal operating portion;
   (b) drilling an opening in the distal operating portion adjacent the working element;
   (c) milling the shaft sufficiently to provide a groove extending on an outer surface of the shaft from the opening in a direction toward a proximal portion of the surgical instrument; and
   (d) coupling at least a portion of a fiberoptic assembly in the opening and the groove of the surgical instrument.

39. The method of claim 38 wherein the fiberoptic assembly has a field-of-view and the distal end of the fiberoptic assembly is inserted into the opening sufficiently to place at least a portion of the working element within the field-of-view, and a further portion of the fiberoptic assembly is coupled within the groove.

40. A surgical instrument for use with a viewing system comprising:
   (a) an elongated shaft having proximal and distal portions with the proximal and distal portions having axes being displaceable with respect to each other;
   (b) a handle member mounted on the proximal portion of the shaft and offset from the shaft;
   (c) a working element disposed on the distal portion of the shaft for manipulating tissue during the course of a surgical procedure;
   (d) an elongated fiberoptic assembly including image fibers having a proximal end and a distal end with an objective lens mounted on the distal end of the image fibers for defining a predetermined field-of-view;
   (e) coupling means at the proximal end of the image fibers for coupling same to the viewing system;
   (f) a proximal mount mounting the fiberoptic assembly to the proximal potion of the shaft with the assembly extending along at least a portion of the handle member; and
   (g) a distal mount mounting the fiberoptic assembly to the distal portion of the shaft with the distal end of the image fibers positioned with a predetermined portion of the working element within the field-of-view of the fiberoptic assembly.

41. The surgical instrument of claim 40 wherein the shaft is bendable.

42. The surgical instrument of claim 40 wherein the proximal and distal mounts include a tube extending along the shaft.

43. The surgical instrument of claim 40 wherein the proximal mount includes a proximal tube extending along the proximal portion of the shaft and the distal mount includes a distal tube extending along the distal portion of the shaft.

44. The surgical instrument of claim 43 wherein the proximal and distal tubes are spaced.

45. The surgical instrument of claim 40 wherein the proximal mount removably mounts the fiberoptic assembly to the proximal portion of the shaft, and the distal mount removably mounts the fiberoptic assembly to the distal portion of the shaft.

46. The surgical instrument of claim 40 wherein the proximal and distal mounts are coupled to the exterior of the shaft.

47. The surgical instrument of claim 40 wherein the fiberoptic assembly is also mounted on the handle member.

48. The surgical instrument of claim 40 further including an illumination fiber mounted to the distal portion of the shaft having a distal end positioned to project light in the field-of-view.

49. The surgical instrument of claim 40 wherein the fiberoptic assembly includes an illumination fiber.

50. The surgical instrument of claim 40 wherein the shaft includes actuating means operatively coupled to the working element.

* * * * *